(12) United States Patent
Heidenfelder et al.

(10) Patent No.: US 6,458,342 B1
(45) Date of Patent: Oct. 1, 2002

(54) USE OF SUNSCREEN COMBINATIONS COMPRISING, AS ESSENTIAL CONSTITUENT, 2,2'-P-PHENYLENEBIS (3,1-BENZOXAZIN-4-ONE) AS PHOTOSTABLE UV FILTERS IN COSMETIC AND PHARMACEUTICAL PREPARATIONS

(75) Inventors: Thomas Heidenfelder, Römerberg-Mechtersheim; Kristin Tiefensee, Bad Duerkheim; Thomas Wünsch, Speyer, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/015,561

(22) Filed: Dec. 17, 2001

(30) Foreign Application Priority Data

Dec. 2, 2000 (DE) .......................... 100 63 946

(51) Int. Cl.[7] .............. A61K 7/42; A61K 7/44; A61K 7/00
(52) U.S. Cl. .......................... 424/59; 424/60; 424/400; 424/401
(58) Field of Search ............... 424/59, 60, 400, 424/401

(56) References Cited

U.S. PATENT DOCUMENTS

| | | | |
|---|---|---|---|
| 4,387,089 A | 6/1983 | De Polo | 424/59 |
| 4,514,231 A | 4/1985 | Kerner et al. | |
| 5,234,681 A | 8/1993 | Yoshida et al. | 424/59 |
| 6,120,757 A | 9/2000 | Dubief et al. | 424/70 |
| 6,238,649 B1 | 5/2001 | Habeck | 424/59 |

FOREIGN PATENT DOCUMENTS

| | | |
|---|---|---|
| DE | 33 14746 | 10/1984 |
| DE | 197 26 121 | 12/1998 |
| EP | 0 251 398 | 7/1988 |
| EP | 0 416 837 | 3/1991 |
| EP | 0 895 776 | 2/1999 |
| EP | 0 916 335 | 5/1999 |
| EP | 0 920 859 | 6/1999 |
| EP | 199 17 906 | 10/2000 |
| FR | 2 440 933 | 6/1980 |
| GB | 2 038 807 | 7/1980 |

*Primary Examiner*—Shelley A. Dodson
(74) *Attorney, Agent, or Firm*—Keil & Weinkauf

(57) ABSTRACT

Sunscreen combinations which comprise
  A) effective amounts of a compound of formula I

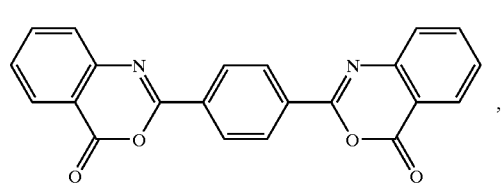

and
  B) effective amounts of one or more compounds selected from a group consisting of: zinc oxide, titanium oxide and the compounds of formulae II to XVI which are specified in the description,
are suitable as photostable UV filters in cosmetic and pharmaceutical compositions for protecting human skin or human hair against solar rays. The combinations are optionally used together with other conventional UV absorbing ingredients which are known per se for cosmetic and pharmaceutical compositions.

4 Claims, No Drawings

USE OF SUNSCREEN COMBINATIONS COMPRISING, AS ESSENTIAL CONSTITUENT, 2,2'-P-PHENYLENEBIS (3,1-BENZOXAZIN-4-ONE) AS PHOTOSTABLE UV FILTERS IN COSMETIC AND PHARMACEUTICAL PREPARATIONS

The invention relates to the use of sunscreen combinations which comprise, as constituent which absorbs in the UV-A region, 2,2'-p-phenylenebis(3,1-benzoxazin-4-one), and at least one further sunscreen which absorbs in the UV-A region, in the UV-B region or in both regions, chosen from a group defined in detail below as photostable UV filter combination in cosmetic and pharmaceutical preparations for protecting the human epidermis or human hair against UV radiation, specifically in the range from 320 to 400 nm.

The sunscreens employed in cosmetic and pharmaceutical preparations have the task of preventing, or at least diminishing the consequences of, harmful effects of sunlight on the human skin. However, these sunscreens also serve to protect other ingredients from decomposition or degradation by UV radiation. In hair cosmetic formulations the aim is to reduce damage to the keratin fibers by UV rays.

The sunlight reaching the surface of the earth has a proportion of UV-B radiation (280 to 320 nm) and of UV-A radiation (>320 nm), which are directly adjacent to the visible light region. The effect on the human skin becomes evident, particularly in the case of UV-B radiation, from sunburn. Accordingly, the industry offers a relatively large number of substances which absorb UV-B radiation and thus prevent sunburn.

Dermatological investigations have now shown that UV-A radiation is also perfectly capable of causing skin damage and allergies by, for example, damaging the keratin or elastin. This reduces the elasticity and water storage capacity of the skin, i.e. the skin becomes less supple and tends to form wrinkles. The noticeably high incidence of skin cancer in regions where solar radiation is strong shows that damage to the genetic information in the cells is evidently also caused by sunlight, specifically by UV-A radiation. All these findings would therefore suggest the need to develop efficient filter substances for the UV-A region.

There is a growing demand for sunscreens for cosmetic and pharmaceutical preparations which can be used in particular as UV-A filters and whose absorption maxima ought therefore to be in the range from about 320 to 380 nm. In order to achieve the required effect using the minimum amount, sunscreens of this type ought additionally to have a high specific absorbance. Furthermore, sunscreens for cosmetic products must also meet a large number of other requirements, for example good solubility in cosmetic oils, high stability of the emulsions produced with them, toxicological acceptability, and low intrinsic odor and low intrinsic color.

Another requirement which sunscreens must meet is adequate photostability. However, this is only inadequately ensured, if at all, with the UV-A-absorbing sunscreens hitherto available.

French Patent No. 2 440 933 describes 4-(1,1-dimethylethyl)-4'-methoxydibenzoylmethane as a UV-A filter. It is proposed to combine this specific UV-A filter, which is sold by GIVAUDAN under the name "PARSOL 1789", with various UV-B filters in order to absorb all UV rays having a wavelength from 280 to 380 nm.

However, this UV-A filter does not have sufficient photochemical stability, when used alone or in combination with UV-B filters, to ensure sustained protection of the skin during sunbathing for prolonged periods, which means that repeated applications at regular and short intervals are required if effective protection of the skin against all UV rays is desired.

For this reason, EP-A-0 514 491 discloses the stabilization of the insufficiently photostable UV-A filters by adding 2-cyano-3,3-diphenylacrylic esters which themselves act as filters in the UV-B region.

It has furthermore already been proposed in EP-A-0 251 398 and EP-A-0 416 837 to combine chromophores absorbing UV-A radiation and UV-B radiation in one molecule using a connecting member. This has the disadvantage that firstly a free combination of UV-A and UV-B filters in the cosmetic preparation is no longer possible, and that difficulties in the chemical linking of the chromophores allow only certain combinations.

It is an object of the present invention to propose sunscreens for cosmetic and pharmaceutical purposes which absorb in the UV-A region with high absorbance, which are photostable, have low intrinsic color, i.e. a sharp band structure, and are soluble in oil or water, depending on the substituent.

We have found that this object can be achieved advantageously by certain sunscreen combinations.

Accordingly, this object is achieved according to the invention by the use of sunscreen combinations comprising a A) compound absorbing essentially in the UV-A region and B) further compounds absorbing in the UV-A region, in the UV-B region and in both regions, where the constituent absorbing in the UV-A region consists of A) effective amounts of the compound of the formula

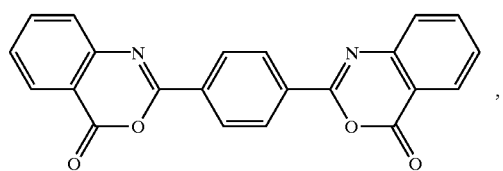

and the constituent

B) comprises effective amounts of one or more compounds chosen from the group consisting of Ba) the compound of the formula II

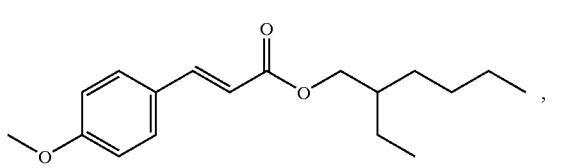

Bb) the compound of the formula III

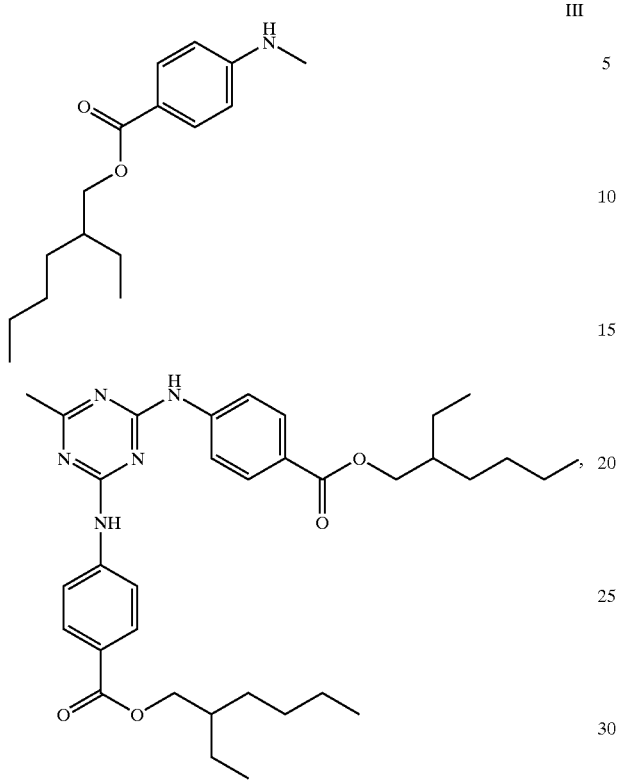

Bc) the compound of the formula IV

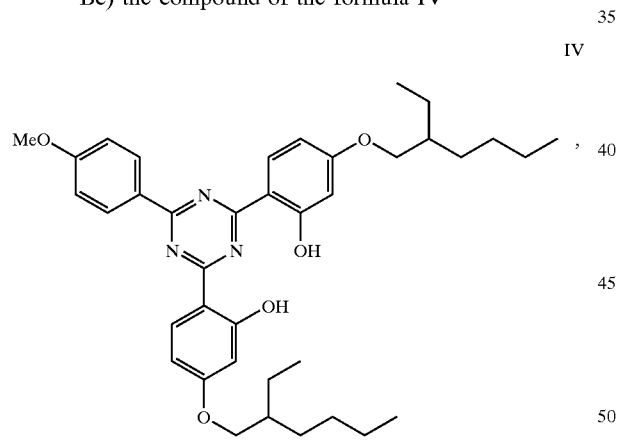

Bd) the compound of the formula V

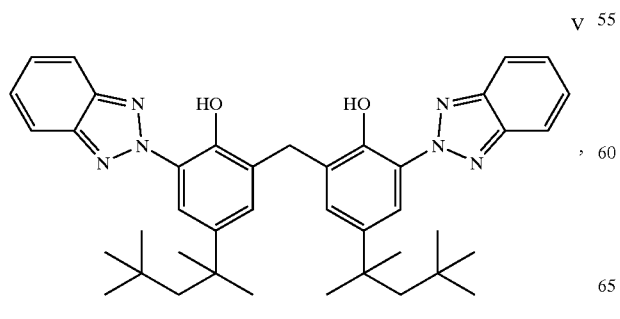

Be) the compound of the formula VI

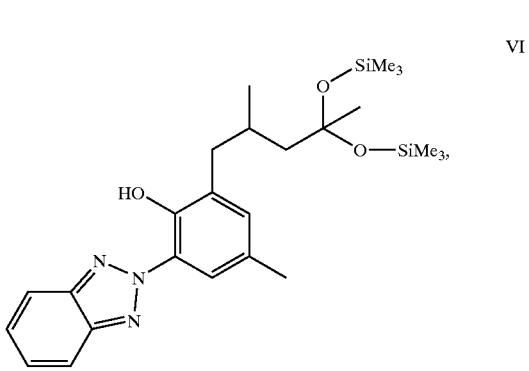

Bf) an organosiloxane benzalmalonate of the formula VIIa

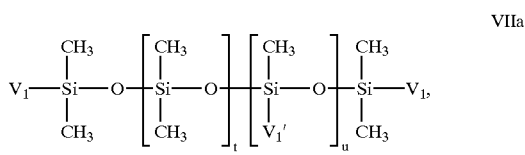

in which
$V_1'$ is the group

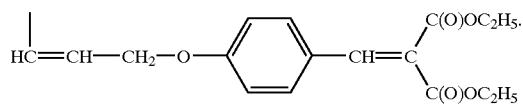

$V_1$ is a methyl group or $V_1'$, or of the formula VIIb

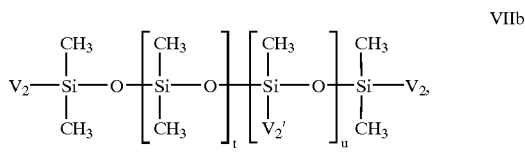

in which $V_2'$ is the group of the structure

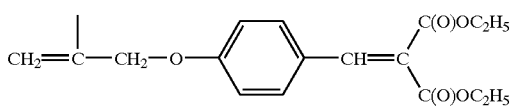

$V_2$ is a methyl group or $V_2'$,
or mixtures of compounds of the formulae VIIa and VIIb,
where t is a value up to 100 and u is a value up to 20, with the proviso that u=0 if $V_1=V_1'$ and/or $V_2=V_2'$, and u is a value from 1 to 20 if $V_1=CH_3$ and/or $V_2=CH_3$, Bg) the compound of the formula VIII

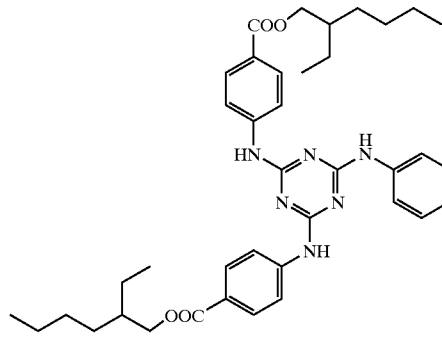

Bh) the compound of the formula IX

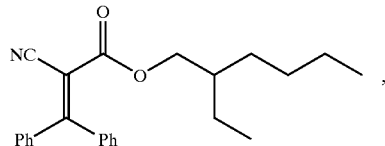

Bi) the compound of the formula X

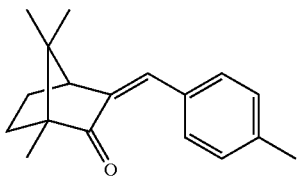

Bj) the compound of the formula XI

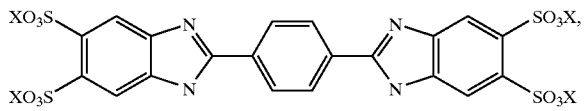

in which X is hydrogen, sodium, potassium, ammonium or triethanolammonium,

Bk) the compound of the formula XII

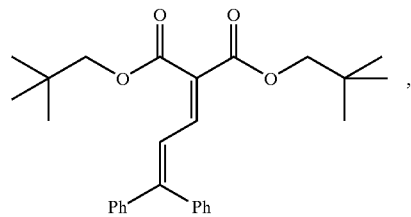

Bl) the compound of the formula XIII

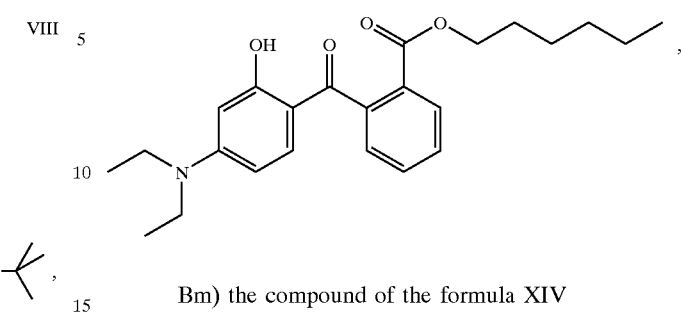

Bm) the compound of the formula XIV

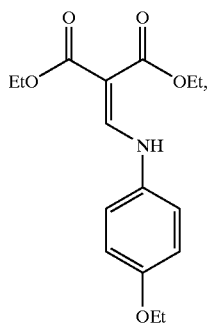

Bn) the compound of the formula XV

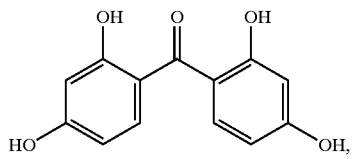

Bo) the compound of the formula XVI

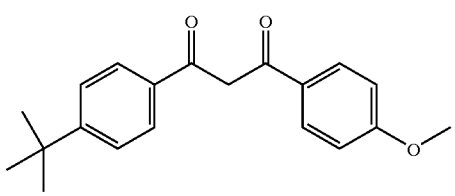

and

Bp) zinc oxide (XVII) and/or titanium dioxide (XVIII)

as photostable UV filters in cosmetic and pharmaceutical preparations for protecting human skin or human hair against solar rays, optionally together with other compounds which absorb in the UV region and are known per se for cosmetic and pharmaceutical preparations.

The sunscreen combination of the compounds (A) and (B) can be used alone or in combination with other compounds which absorb in the UV region, although at least effective amounts of the compounds (A) and (B) should be present in the sunscreen preparations. "Effective amounts of the compounds (A) and of the compounds (B)" means generally in each case at least 0.1% by weight, in each case based on the cosmetic preparation.

In the sunscreen combinations according to the invention, the amount of compounds which absorb in the UV-B region usually predominates. Accordingly, the content of the compound (A) which absorbs in the UV-A region is generally 5 to 50% by weight, preferably 10 to 25% by weight, in each case based on sunscreen combination of (A) and (B).

The sunscreen combinations are characterized by their high photostability, and the preparations prepared with the sunscreen combinations by their pleasant feel on the skin.

The compound of the formula I has the CAS No. 018600-59-4 and is known under the name Cyasorb® 3638 (Cyasorb) as stabilizer for plastics. In addition, it is described in U.S. Pat. No. 5,234,681 as a constituent of cosmetic preparations. Moreover, column 5 of said patent specification, lines 54 to 58, mentions that it is possible to use the compound group to which the compound of the formula I belongs, together with known ultraviolet absorbers. However, it could not be concluded from these statements that particularly advantageous combinations can be obtained with certain selected UV absorbers.

The compounds (B) are all known and are characterized in more detail below:

Ba) The compound of the formula II has the CAS No. 5466-77-3 and is sold under the trade name Uvinul® MC80 (BASF).

Bb) The compound of the formula III has the CAS No. 88122-99-0 and is sold under the trade name Uvinul® T150 (BASF).

Bc) The compound of the formula IV has the CAS No. 187393-00-6.

Bd) The compound of the formula V has the CAS No. 103597-45-1 and is sold under the trade name Tinosorb® M (CIBA).

Be) The compound of the formula VI has the CAS No. 155633-54-8 and is known under the trade name Mexoryl® XL (CHIMEX).

Bf) The compounds or mixtures of compounds of the formula VII are known from EP-A 0920859. Of the compounds of the formulae VIIa and/or VIIb, those with the CAS numbers 208391-15-5, 208391-15-5D, 177955-90-7, 177955-90-7D and 177995-90-7DP are particularly suitable.

Bg) The compound of the formula VIII has the CAS No. 154702-15-5 and is sold under the trade name Uvasorb® HEB (BV Sigma).

Bh) The compound of the formula IX has the CAS No. 6197-30-4 and is sold under the trade name Uvinul® N539 (BASF).

Bi) The compound of the formula X has the CAS No. 36861-47-9 and is sold under the trade name Uvinul MBCs 95 (BASF).

Bj) The compound of the formula XI has the CAS No. 180898-37-7 (Haarmann & Reimer).

Bk) The compound of the formula XII is known from EPA 916 335.

Bl) The compound of the formula XIII is known from DE-A 19917906.

Bm) The compound of the formula XIV is known from EP-A 895776.

Bn) The compound of the formula XV has the CAS No. 131-55-5 and is sold under the trade name Uvinuls® D50 (BASF).

Bo) The compound of the formula XVI has the CAS No. 70356-09-1.

Bp) Suitable as ZnO and TiO$_2$ are the pigments used in standard commercial manner for cosmetic preparations.

In the sunscreen combinations to be used according to the invention, it is possible for not only individual compounds (Ba) to (Bp) to be present, but also mixtures of two or more of these compounds.

The present invention further provides cosmetic and pharmaceutical preparations which have 0.1 to 40% by weight, preferably 1 to 25% by weight, based on the total amount of the cosmetic and pharmaceutical preparation, of a sunscreen combination comprising a A) compound absorbing essentially in the UV-A region and B) further compounds absorbing in the UV-A region, in the UV-B region and over both regions, where the constituent absorbing in the UV-A region consists of A) effective amounts of the compound of the formula

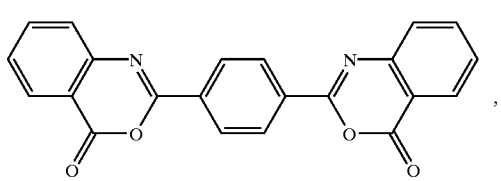

I and the constituent

B) comprises effective amounts of one or more compounds chosen from the group consisting of Ba) the compound of the formula II

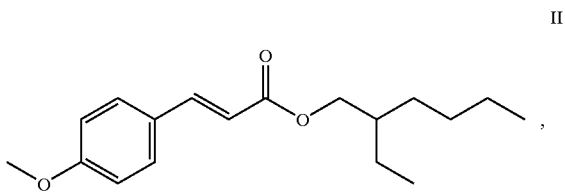

II

Bb) the compound of the formula III

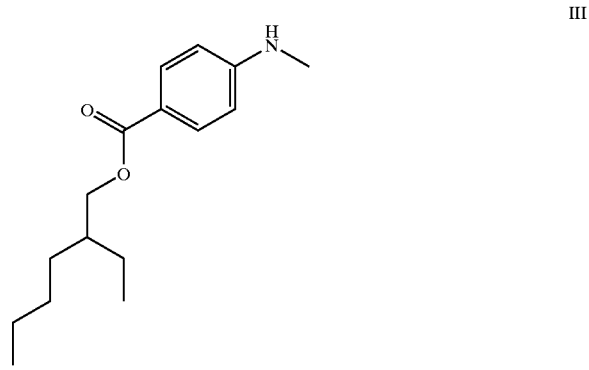

III

Bc) the compound of the formula IV

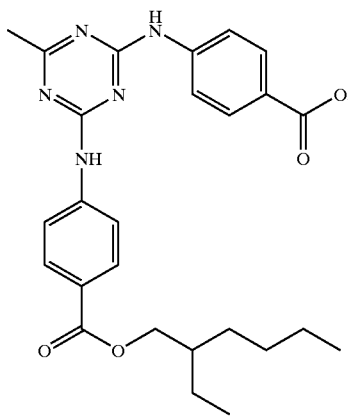

Bd) the compound of the formula V

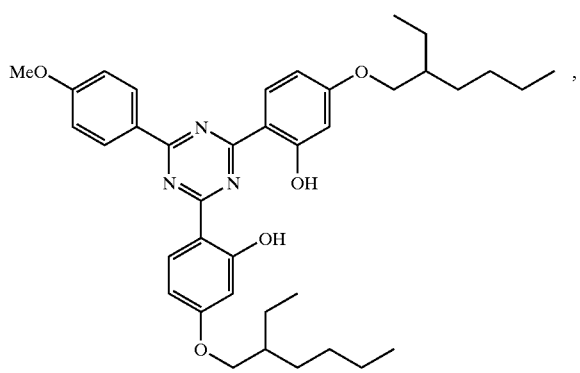

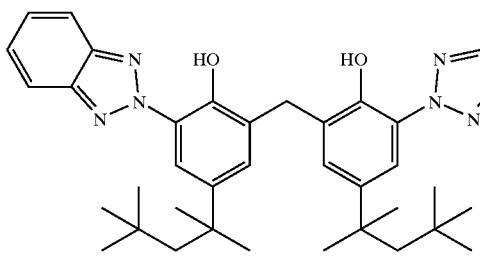

Be) the compound of the formula VI

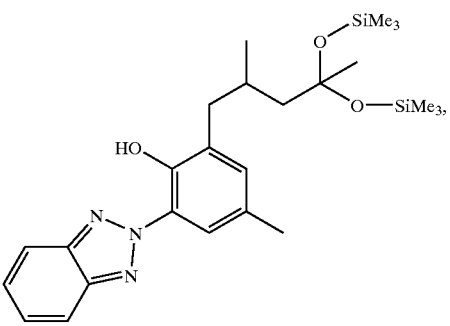

Bf) an organosiloxane benzalmalonate of the formula VIIa

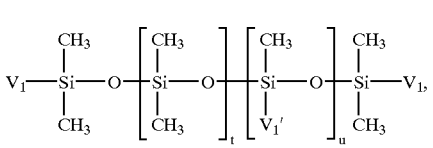

in which
V$_1$' is the group

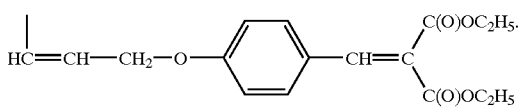

V$_1$ is a methyl group or V$_1$', or of the formula VIIb

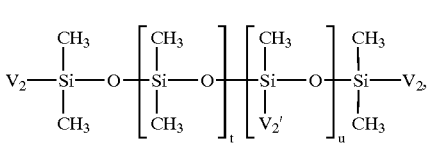

in which V$_2$' is the group of the structure

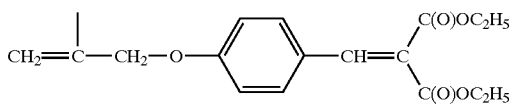

V$_2$ is a methyl group or V$_2$'
or mixtures of compounds of the formulae VIIa and VIIb,
where t is a value up to 100 and u is a value up to 20, with the proviso that u=0 if V$_1$=V$_1$' and/or V$_2$=V$_2$', and u is a value from 1 to 20 if V$_1$=CH$_3$ and/or V$_2$=CH$_3$, Bg) the compound of the formula VIII

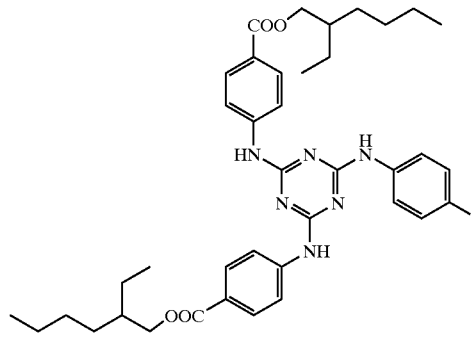

Bh) the compound of the formula IX

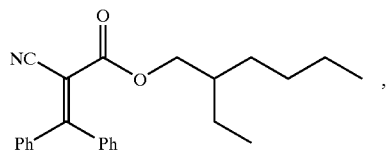

Bi) the compound of the formula X

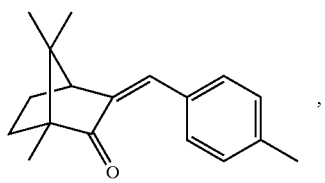

Bj) the compound of the formula XI

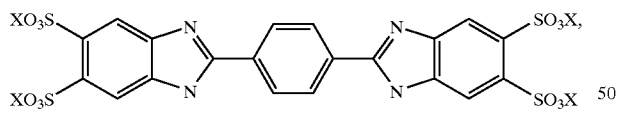

in which X is hydrogen, sodium, potassium, ammonium or triethanolammonium,

Bk) the compound of the formula XII

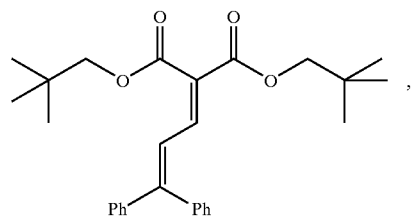

Bl) the compound of the formula XIII

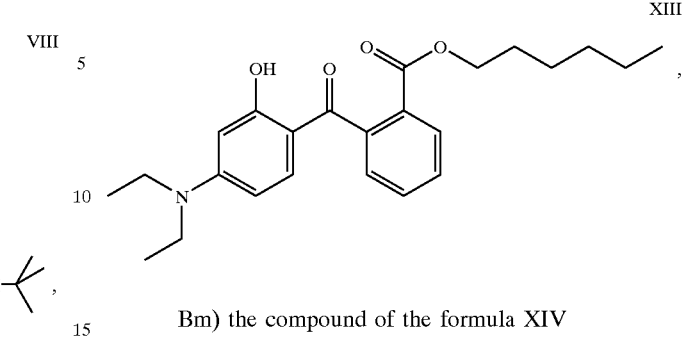

Bm) the compound of the formula XIV

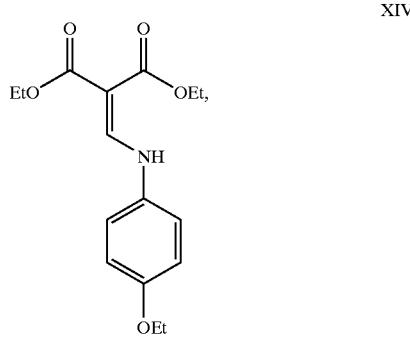

Bn) the compound of the formula XV

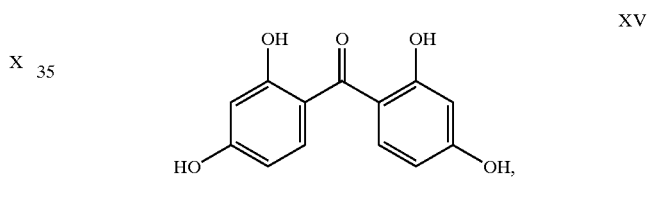

Bo) the compound of the formula XVI

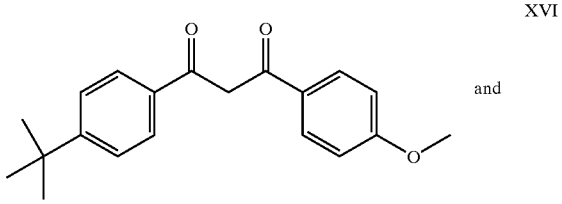

Bp) zinc oxide (XVII) and/or titanium dioxide (XVIII)

as photostable UV filters in cosmetic and pharmaceutical preparations for protecting human skin or human hair against solar rays, optionally together with other compounds which absorb in the UV region and are known per se for cosmetic and pharmaceutical preparations, optionally together with further compounds which absorb in the UV-A and UV-B regions and which are known per se for cosmetic and pharmaceutical preparations, as sunscreens, where the UV-A-absorbing compounds are generally used in a lesser amount than the UV-B-absorbing compounds.

The sunscreen-containing cosmetic and pharmaceutical preparations are, as a rule, based on a carrier which comprises at least one oil phase. However, preparations based exclusively on water are also possible if compounds with hydrophilic substituents are used. Accordingly, oils, oil-in-water and water-in-oil emulsions, creams and pastes, protective lipstick compositions or fat-free gels are suitable.

Suitable emulsions are inter alia also O/W macroemulsions, O/W microemulsions or O/W/O emulsions containing the compound of the formula I in dispersed form, the emulsions being obtainable by phase inversion technology, as in DE-A-197 26 121. Here, the particle size of the compound of the formula I is chosen such that it is 3 $\mu$m or less, preferably 1 $\mu$m or less.

Conventional cosmetic auxiliaries which may be suitable as additives are, for example, coemulsifiers, fats and waxes, stabilizers, thickeners, biogenic active ingredients, film formers, fragrances, dyes, pearlizing agents, preservatives, pigments, electrolytes (e.g. magnesium sulfate) and pH regulators. Suitable and preferred coemulsifiers are known W/O and O/W emulsifiers such as polyglycerol esters, sorbitan esters or partially esterified glycerides. Typical examples of fats are glycerides; waxes which may be mentioned are, inter alia, beeswax, paraffin wax or microwaxes, possibly in combination with hydrophilic waxes. Stabilizers which can be employed are metal salts of fatty acids such as, for example, magnesium stearate, aluminum stearate and/or zinc stearate. Examples of suitable thickeners are crosslinked polyacrylic acids and derivatives thereof, polysaccharides, in particular xanthan gum, guar guar, agar agar, alginates and tyloses, carboxymethylcellulose and hydroxyethylcellulose, also fatty alcohols, monoglycerides and fatty acids, polyacrylates, polyvinyl alcohol and polyvinylpyrrolidone. Examples of biogenic active ingredients are plant extracts, protein hydrolyzates and vitamin complexes.

Examples of customary film formers are hydrocolloids such as chitosan, microcrystalline chitosan or quaternized chitosan, polyvinylpyrrolidone, vinylpyrrolidone/vinyl acetate copolymers, polymers of the acrylic acid series, quaternary cellulose derivatives and similar compounds. Examples of suitable preservatives are formaldehyde solution, p-hydroxybenzoate or sorbic acid. Examples of suitable pearlizing agents are glycol distearic esters such as ethylene glycol distearate, but also fatty acids and fatty acid monoglycol esters. Dyes which can be used are the substances suitable and approved for cosmetic purposes, as listed, for example, in the publication "Kosmetische Färbemittel" [Cosmetic Colorants] from the Farbstoffkommission der Deutschen Forschungsgemeinschaft [Dyes Commission of the German Research Society], published by Verlag Chemie, Weinheim, 1984. These dyes are normally employed in a concentration of from 0.001 to 0.1% by weight, based on the total mixture.

An additional content of antioxidants is generally preferred. Thus, it is possible to use as favorable antioxidants all antioxidants which are customary or suitable for cosmetic and/or dermatological applications.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. B-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl, and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximines, buthionine sulfones, penta-, hexa-, heptathionine sulfoximine) in very low tolerated doses (e.g. pmol to $\mu$mol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives thereof (e.g. ascorbyl palmitate, Mg ascorbylphosphate, ascorbylacetate), tocopherol and derivatives (e.g. vitamin E acetate, tocotrienol), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide).

The amount of the abovementioned antioxidants (one or more compounds) in the preparations is preferably from 0.001 to 30% by weight, particularly preferably from 0.05 to 20% by weight, in particular from 1 to 10% by weight, based on the total weight of the preparation.

If vitamin E and/or derivatives thereof are the antioxidant(s), it is advantageous to choose their particular concentration from the range 0.001 to 10% by weight, based on the total weight of the formulation.

If vitamin A and/or derivatives thereof, or carotenoids are the antioxidant(s), it is advantageous to choose their particular concentration from the range 0.001 to 10% by weight, based on the total weight of the formulation.

Customary oil components in cosmetics are, for example, paraffin oil, glyceryl stearate, isopropyl myristate, diisopropyl adipate, cetylstearyl 2-ethylhexanoate, hydrogenated polyisobutene, vaseline, caprylic/capric triglycerides, microcrystalline wax, lanolin and stearic acid.

The total amount of auxiliaries and additives can be from 1 to 80% by weight, preferably from 6 to 40% by weight, and the nonaqueous fraction ("active substance") can be from 20 to 80% by weight, preferably from 30 to 70% by weight, based on the compositions. The compositions can be prepared in a manner known per se, i.e. for example by hot, cold, hot-hot/cold or PIT emulsification. This is a purely mechanical process; no chemical reaction takes place.

Such sunscreen preparations can accordingly be in liquid, paste or solid form, for example as water-in-oil creams, oil-in-water creams and lotions, aerosol foam creams, gels, oils, marking pencils, powders, sprays or alcoholic-aqueous lotions.

Finally, it is also possible to co-use other substances which asorb in the UV region and are known per se provided they are stable in the overall system of the combination of UV filters to be used according to the invention.

Suitable UV filter substances which can be additionally used with the sunscreen combinations to be used according to the invention are any UV-A and UV-B filter substances. Examples which may be mentioned are:

| No. | Substance | CAS No. (=acid) |
|---|---|---|
| 1 | 4-Aminobenzoic acid | 150-13-0 |
| 2 | 3-(4'-Trimethylammonium)benzylidenebornan-2-one methylsulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)-bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Ethylhexyl 4-methoxycinnamate | 5466-77-3 |
| 11 | 2-Hydroxy-4-methoxybenzophenone-5-sulfonic acid (sulisobenzone) and the sodium salt | 4065-45-6 |
| 12 | 3-(4'-Sulfo)benzylidenebornan-2-one and salts | 58030-58-6 |
| 13 | 3-Benzylidenebornan-2-one | 16087-24-8 |
| 14 | 1-(4'-Isopropylphenyl)-3-phenylpropane-1,3-dione | 63260-25-9 |
| 15 | 4-Isopropylbenzyl salicylate | 94134-93-7 |
| 16 | 3-Imidazol-4-yl-acrylic acid and its ethyl ester | 104-98-3 |
| 17 | Ethyl 2-cyano-3,3-diphenylacrylate | 5232-99-5 |
| 18 | Menthyl o-aminobenzoate or: 5-methyl-2-(1-methylethyl) 2-aminobenzoate | 134-09-8 |
| 19 | Glyceryl p-aminobenzoate or: 1-glyceryl 4-aminobenzoate | 136-44-7 |
| 20 | 2,2'-Dihydroxy-4-methoxybenzophenone (dioxybenzone) | 131-53-3 |
| 21 | 2-Hydroxy-4-methoxy-4-methylbenzophenone (mexenone) | 1641-17-4 |
| 22 | Triethanolamine salicylate | 2174-16-5 |
| 23 | Dimethoxyphenylglyoxalic acid or: sodium 3,4-dimethoxyphenylglyoxalate | 4732-70-1 |
| 24 | 3-(4'-Sulfo)benzylidenebornan-2-one and its salts | 56039-58-8 |

Furthermore, the cosmetic and dermatological preparations according to the invention can advantageously comprise further inorganic pigments based on metal oxides and/or other metal compounds which are insoluble or virtually insoluble in water, in particular the oxides of iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and admixtures of such oxides.

For the purposes of the present invention, it is particularly advantageous, but not obligatory, for the inorganic pigments to be present in hydrophobic form, i.e. to have been surface-treated to repel water. This surface treatment can involve providing the pigments with a thin hydrophobic layer in a manner known per se, as described in DE-A-33 14 742.

To protect human hair against UV rays, the sunscreen combinations to be used according to the invention can be incorporated into shampoos, lotions, gels, hairsprays, aerosol foam creams or emulsions in concentrations of from 0.1 to 10% by weight, preferably from 1 to 7% by weight. The respective formulations can be used, inter alia, for washing, coloring and for styling the hair.

The sunscreen combinations to be used according to the invention are readily soluble in cosmetic oils and can be easily incorporated into cosmetic formulations. The emulsions prepared with the novel sunscreen combinations are characterized in particular by their high stability, the sunscreen combinations themselves are characterized by their high photostability, and the preparations prepared with the sunscreen combinations are characterized by their pleasant feel on the skin.

The UV filter action of the sunscreen combinations to be used according to the invention can also be utilized for stabilizing active ingredients and auxiliaries in cosmetic and pharmaceutical formulations.

The examples below illustrate the use of the novel sunscreen combinations in more detail.

EXAMPLES

Example 1

Standardized Method to Determine Photostability (Sun Test)

A 5% strength by weight alcoholic solution of the sunscreen to be tested is applied, using an Eppendorf pipette (20 μl), to the milled area on a small glass plate. Owing to the presence of the alcohol, the solution distributes uniformly on the roughened glass surface. The amount applied corresponds to the amount of sunscreen required to obtain an average sun protection factor in sun creams. In the test, 4 small glass plates are irradiated each time. The evaporation time and the irradiation each last for 30 minutes. The small glass plates are cooled slightly during the irradiation by a water cooling system located at the base of the sun test apparatus. The temperature inside the sun test apparatus during the irradiation is 40° C. After the samples have been irradiated, they are washed with ethanol into a dark 50 ml graduated flask and measured using a photometer. The blank samples are applied in the same way to small glass plates and evaporated at room temperature for 30 minutes. Like the other samples, they are washed off with ethanol and diluted to 100 ml and measured.

General Procedure for Preparing Emulsions for Cosmetic Purposes

All of the oil-soluble constituents are heated to 85° C. in a stirred vessel. When all the constituents are molten or are present as liquid phase, the aqueous phase is incorporated with homogenization. The emulsion is cooled to about 40° C. with stirring, is perfumed and homogenized, and is then cooled to 25° C. with continuous stirring.

Preparations

Example 2

Lip Care Composition

Mass Content (% by Weight)

ad 100 Eucerinum anhydricum
10.00 glycerol
filter combination consisting of
   5.00 (I)
   8.00 (II)
   10.00 $TiO_2$ (XVIII)
   5.00 ZnO$_2$ (XVII)
4.00 castor oil
4.00 pentaerythrityl stearate/caprate/caprylate/adipate
3.00 glyceryl stearate SE
2.00 beeswax
2.00 microcrystalline wax
2.00 quaternium-18 bentonite
1.50 PEG-45/dodecyl glycol copolymer

Example 3
Lip Care Composition

Mass Content (% by Weight)

ad 100 Eucerinum anhydricum
10.00 glycerol
filter combination consisting of
  1.00 (I)
  8.00 (II)
  4.00 (V)
  10.00 $TiO_2$ (XVIII)
  5.00 $ZnO_2$ (XVII)
4.00 castor oil
4.00 pentaerythrityl stearate/caprate/caprylate/adipate
3.00 glyceryl stearate SE
2.00 beeswax
2.00 microcrystalline wax
2.00 quaternium-18 bentonite
1.50 PEG-45/dodecyl glycol copolymer

Example 4
Sunblocker Composition Containing Micropigments

Mass content (% by Weight)

ad 100 water
6.00 PEG-7 hydrogenated castor oil
filter combination consisting of
  2.00 (I)
  3.00 (V)
  10.00 (II)
  3.00 (X)
  6.00 $TiO_2$ (XVIII)
5.00 mineral oil
5.00 isoamyl p-methoxycinnamate
5.00 propylene glycol
3.00 jojoba oil
2.00 PEG-45/dodecyl glycol copolymer
1.00 dimethicone
0.50 PEG-40 hydrogenated castor oil
0.50 tocopheryl acetate
0.50 phenoxyethanol
0.20 EDTA

Example 5
Sunblocker Composition Containing Micropigments

Mass Content (% by Weight)

ad 100 water
6.00 PEG-7 hydrogenated castor oil
filter combination consisting of
  2.00 (I)
  3.00 (IV)
  10.00 (II)
  3.00 (X)
  6.00 $TiO_2$ (XVIII)
5.00 mineral oil
5.00 isoamyl p-methoxycinnamate
5.00 propylene glycol
3.00 jojoba oil
2.00 PEG-45/dodecyl glycol copolymer
1.00 dimethicone
0.50 PEG-40 hydrogenated castor oil
0.50 tocopheryl acetate
0.50 phenoxyethanol
0.20 EDTA

Example 6
Non-greasy Gel

Mass Content (% by Weight)

ad 100 water
filter combination consisting of
  2.00 (I)
  3.00 (VI)
  8.00 (II)
  1.00 (X)
  7.00 $TiO_2$ (XVIII)
5.00 glycerol
5.00 PEG-25 PABA
0.40 acrylate $C_{10}$-$C_{30}$ alkyl acrylate crosspolymer
0.30 imidazolidinylurea
0.25 hydroxyethylcellulose
0.25 sodium methylparaben
0.20 disodium EDTA
0.15 fragrance
0.15 sodium propylparaben
0.10 sodium hydroxide

Example 7
Non-greasy Gel

Mass Content (% by Weight)

ad 100 water
filter combination consisting of
  1.00 (I)
  4.00 (VI)
  8.00 (II)
  1.00 (X)
  7.00 $TiO_2$ (XVIII)
5.00 glycerol
5.00 PEG-25 PABA
0.40 acrylate $C_{10}$-$C_{30}$ alkyl acrylate crosspolymer
0.30 imidazolidinylurea
0.25 hydroxyethylcellulose
0.25 sodium methylparaben
0.20 disodium EDTA
0.15 fragrance
0.15 sodium propylparaben
0.10 sodium hydroxide

Example 8
Sun Cream

Mass Content (% by Weight)

ad 100 water
filter combination consisting of
  2.00 (I)
  3.00 (XIV)
  8.00 (II)
  1.00 (X)
  8.00 $TiO_2$ (XVIII)
  5.00 $ZnO_2$ (XVII)
6.00 PEG-7 hydrogenated castor oil
6.00 mineral oil
5.00 isopropyl palmitate
0.30 imidazolidinylurea
3.00 jojoba oil
2.00 PEG-45/dodecyl glycol copolymer
0.60 magnesium stearate
0.50 tocopheryl acetate
0.25 methylparaben

Example 9
Sun Cream

Mass Content (% by Weight)

ad 100 water
filter combination consisting of
  3.00 (I)
  3.00 (XI)
  8.00 (II)
  8.00 $TiO_2$ (XVIII)
  5.00 $ZnO_2$ (XVII)
  6.00 PEG-7 hydrogenated castor oil
  6.00 mineral oil
  5.00 isopropyl palmitate
  0.30 imidazolidinylurea
  3.00 jojoba oil
  2.00 PEG-45/dodecyl glycol copolymer
  0.60 magnesium stearate
  0.50 tocopheryl acetate
  0.25 methylparaben
  0.20 disodium EDTA
  0.15 propylparaben

Example 10
Water-resistant Sun Cream

Mass Content (% by Weight)

ad 100 water
filter combination consisting of
  1.00 (I)
  4.00 (IX)
  8.00 (II)
  2.00 (X)
  3.00 $TiO_2$ (XVIII)
  5.00 PEG-7 hydrogenated castor oil
  5.00 propylene glycol
  4.00 isopropyl palmitate
  4.00 caprylic/capric triglyceride
  4.00 glycerol
  3.00 jojoba oil
  1.50 PEG-45/dodecyl glycol copolymer
  1.50 dimethicone
  0.70 magnesium sulfate
  0.50 magnesium stearate
  0.15 fragrance

Example 11
Water-resistant Sun Cream

Mass Content (% by Weight)

ad 100 water
filter combination consisting of
  2.00 (I)
  5.00 (XII)
  2.00 $TiO_2$ (XVIII)
  5.00 PEG-7 hydrogenated castor oil
  5.00 propylene glycol
  4.00 isopropyl palmitate
  4.00 caprylic/capric triglyceride
  4.00 glycerol
  3.00 jojoba oil
  1.50 PEG-45/dodecyl glycol copolymer
  1.50 dimethicone
  0.70 magnesium sulfate
  0.50 magnesium stearate
  0.15 fragrance

Example 12
Sun Milk

Mass Content (% by Weight)

ad 100 water
10.00 mineral oil
6.00 PEG-7 hydrogenated castor oil
5.00 isopropyl palmitate
filter combination consisting of
  3.00 (I)
  5.50 (VIII)
  3.00 caprylic/capric triglyceride
  3.00 jojoba oil
  2.00 PEG-45/dodecyl glycol copolymer
  0.70 magnesium sulfate
  0.60 magnesium stearate
  0.50 tocopheryl acetate
  3.00 glycerol
  0.25 methylparaben
  0.15 propylparaben
  0.05 tocopherol

Example 13
Sun Milk

Mass Content (% by Weight)

ad 100 water
10.00 mineral oil
6.00 PEG-7 hydrogenated castor oil
5.00 isopropyl palmitate
filter combination consisting of
  1.00 (I)
  4.00 (XIV)
  3.50 (II)
  3.00 caprylic/capric triglyceride
  3.00 jojoba oil
  2.00 PEG-45/dodecyl glycol copolymer
  0.70 magnesium sulfate
  0.60 magnesium stearate
  0.50 tocopheryl acetate
  3.00 glycerol
  0.25 methylparaben
  0.15 propylparaben
  0.05 tocopherol

We claim:

1. A method of protecting human hair or epidermis against harmful effects of UV radiation, which comprises treating the hair or the epidermis with an effective amount of a sunscreen combination comprising A) a compound absorbing essentially in the UV-A region, and
B) further compounds absorbing in the UV-A region, in the UV-B region and over both regions, wherein the constituent (A) consists of effective amounts of a compound of formula I

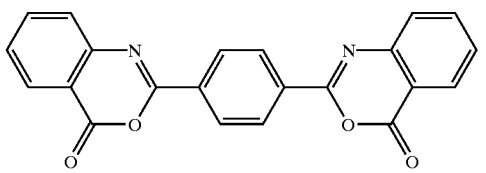

and the constituent B) comprises effective amounts of one or more compounds selected from the group consisting of Ba) a compound of formula II

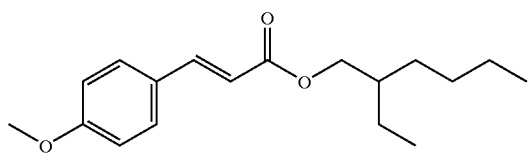

Bb) a compound of formula III

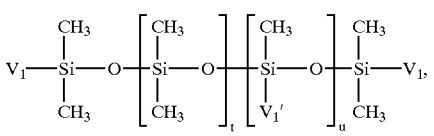

Bc) a compound of formula IV

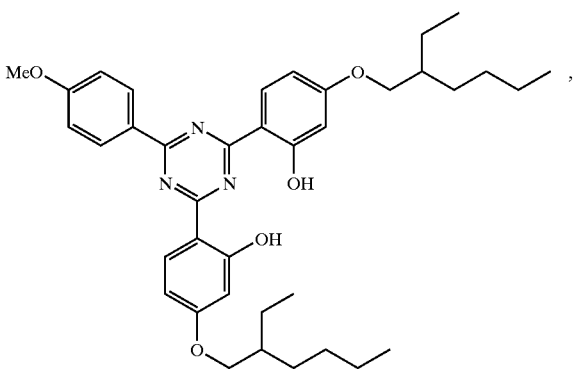

Bd) a compound of formula V

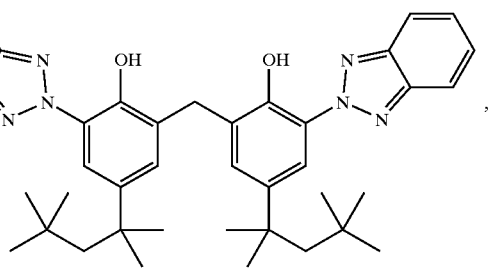

Be) a compound of formula VI

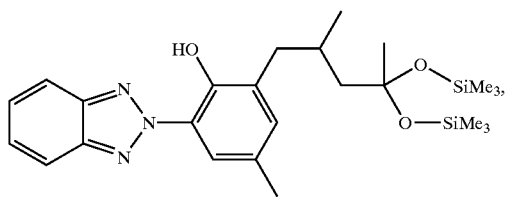

Bf) an organosiloxane benzalmalonate of formula VIIa

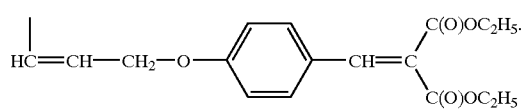

in which $V_1'$ is a group $$HC\!=\!CH\!-\!CH_2\!-\!O\!-\!\!\!\raisebox{0pt}{\phantom{X}}\!\!\!-\!CH\!=\!C\!\!\begin{array}{c}C(O)OC_2H_5\\C(O)OC_2H_5\end{array}$$

$V_1$ is a methyl group or $V_1'$, or an organosiloxane benzalmalonate of formula VIIb

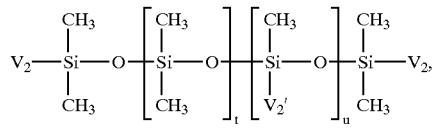
VIIb in which $V_2'$ is a group

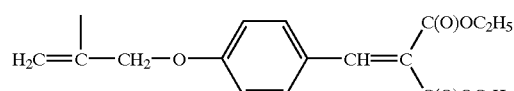

$V_2$ is a methyl group or $V_2'$,
or a mixture of the compounds of formulae VIIa and VIIb,
where t is a value up to 100 and u is a value up to 20, with the proviso that u=0 if $V_1=V_1'$ and/or $V_2=V_2'$, and u is a value from 1 to 20 if $V_1=CH_3$ and/or $V_2=CH_3$, Bg) a compound of formula VIII

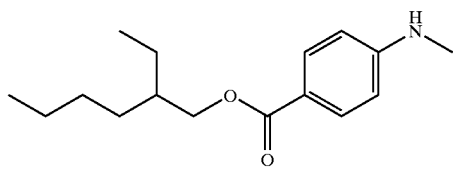
VIII

Bh) a compound of formula IX

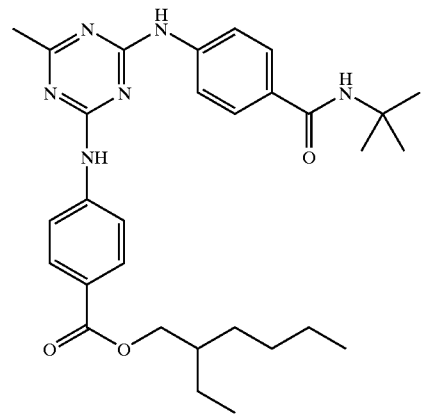
IX

Bi) a compound of formula X

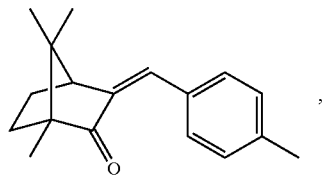
X

Bj) a compound of formula XI

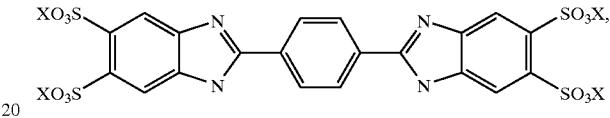
XI in which X is hydrogen, sodium, potassium, ammonium or triethanolammonium, Bk) a compound of formula XII

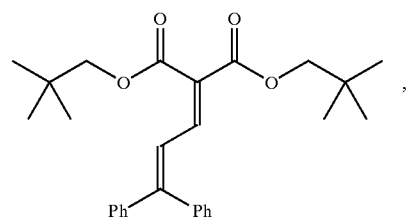
XII

Bl) a compound of formula XIII

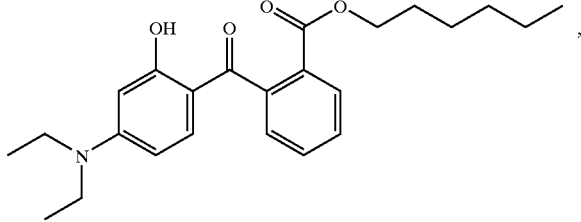
XIII

Bm) a compound of formula XIV

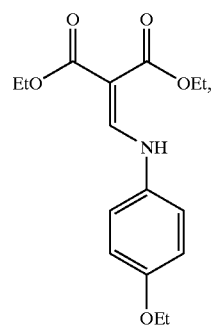
XIV

Bn) a compound of formula XV

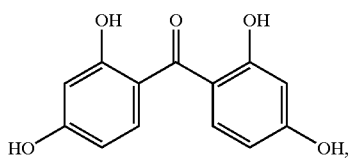

Bo) a compound of formula XVI

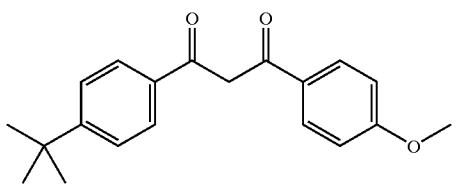

and
Bp) one or both of zinc oxide (XVII) and titanium dioxide (XVIII), optionally in combination with further compounds which absorb in the UV region and are known per se for cosmetic and pharmaceutical preparations.

2. The method of claim 1, wherein the sunscreen combination comprises the constituent (A) in an amount of at least 5% by weight, based on the sunscreen combination.

3. A cosmetic or pharmaceutical composition comprising a sunscreen combination for protecting human epidermis or human hair against UV light in the range from 280 to 400 nm, which composition comprises a cosmetically and pharmaceutically suitable carrier and, as a photostable UV filter, an effective amount of a sunscreen combination comprising A) a compound absorbing essentially in the UV-A region, and
B) further compounds absorbing in the UV-A region, in the UV-B region and over both regions, wherein the constituent (A) consists of effective amounts of a compound of formula I

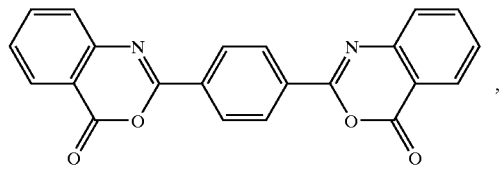

and the constituent B) comprises effective amounts of one or more compounds selected from the group consisting of
Ba) a compound of formula II

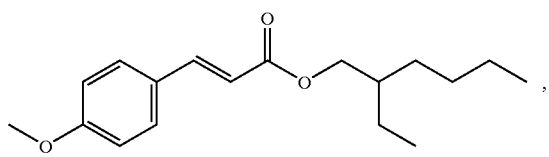

Bb) a compound of formula III

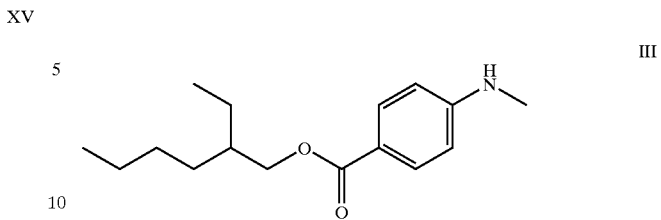

Bc) a compound of formula IV

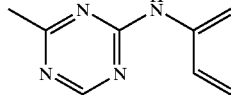

Bd) a compound of formula V

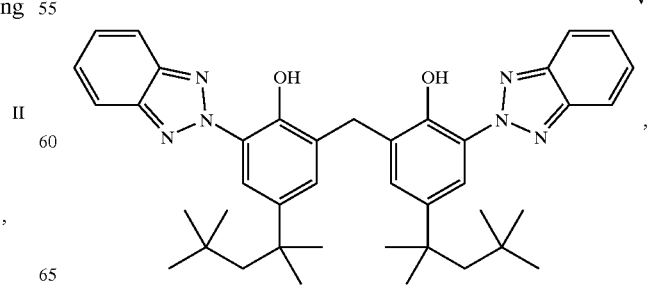

Be) a compound of formula VI

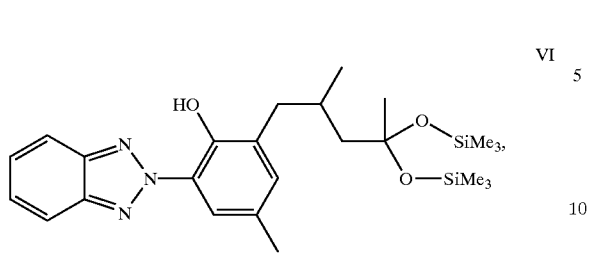

Bf) an organosiloxane benzalmalonate of formula VIIa

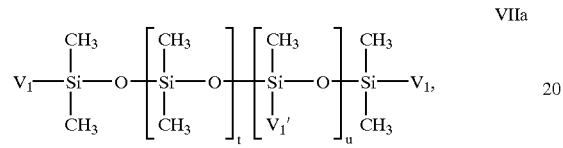

in which $V_1'$ is a group

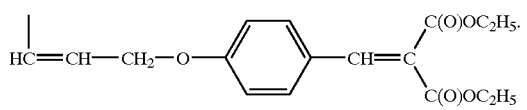

$V_1$ is a methyl group or $V_1'$, or
an organosiloxane benzalmalonate of formula VIIb

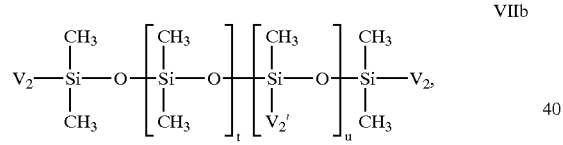

in which $V_2'$ is a group

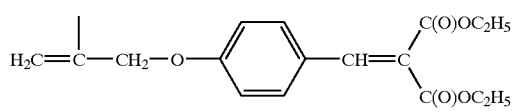

$V_2$ is a methyl group or $V_2'$
or a mixture of the compounds of formulae VIIa and VIIb, where t is a value up to 100 and u is a value up to 20, with the proviso that u=0 if $V_1=V_1'$ and/or $V_2=V_2'$, and u is a value from 1 to 20 if $V_1=CH_3$ and/or $V_2=CH_3$, Bg) a compound of formula VIII

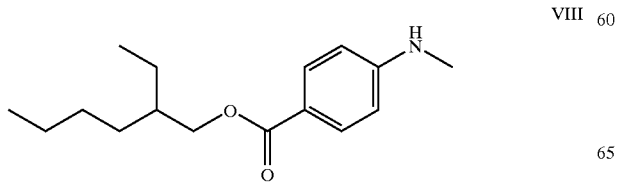

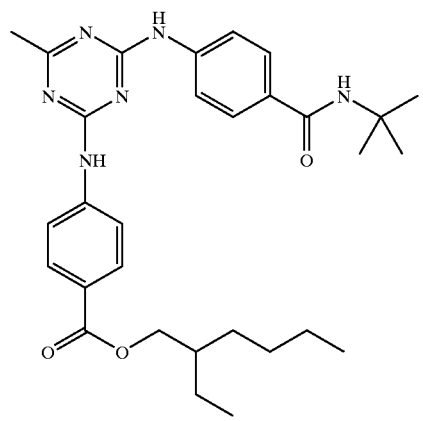

Bh) a compound of formula IX

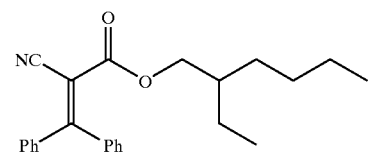

Bi) a compound of formula X

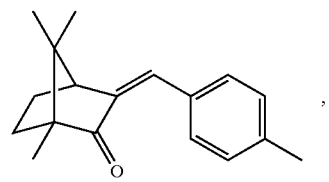

Bj) a compound of formula XI

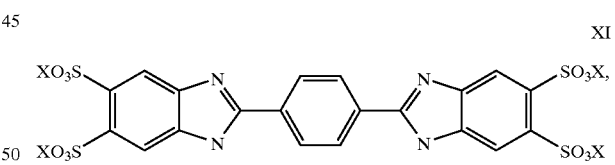

in which X is hydrogen, sodium, potassium, ammonium or triethanolammonium,

Bk) a compound of formula XII

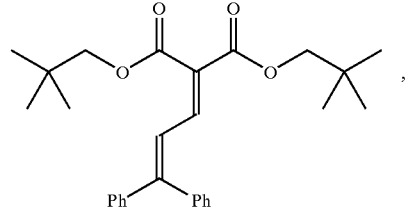

Bl) a compound of formula XIII

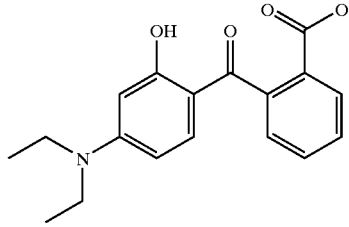

Bm) a compound of formula XIV

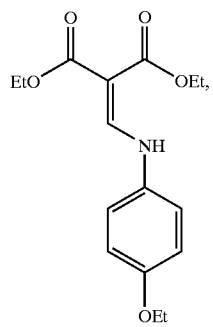

Bn) a compound of formula XV

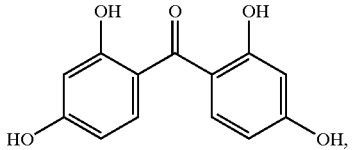

Bo) a compound of formula XVI

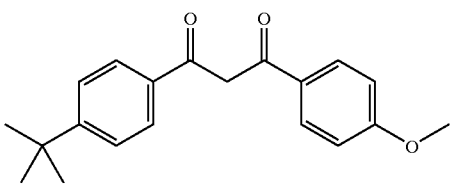

and

Bp) one or both of zinc oxide (XVII) and titanium dioxide (XVIII), optionally in combination with further compounds which absorb in the UV region and which are known per se for cosmetic and pharmaceutical preparations.

4. The cosmetic or pharmaceutical composition defined in claim 3, wherein the sunscreen combination comprises the constituent (A) in an amount of at least 5% by weight, based on the sunscreen combination.

* * * * *

UNITED STATES PATENT AND TRADEMARK OFFICE
CERTIFICATE OF CORRECTION

PATENT NO.    : 6,458,342 B1
DATED         : October 1, 2002
INVENTOR(S)   : Heidenfelder et al.

It is certified that error appears in the above-identified patent and that said Letters Patent is hereby corrected as shown below:

<u>Title page,</u>
Item [30], Foreign Application Priority Data, "Dec. 2, 2000" should be
-- Dec. 20, 2000 --.

Signed and Sealed this

Twenty-eighth Day of January, 2003

JAMES E. ROGAN
*Director of the United States Patent and Trademark Office*